United States Patent
Wang

(10) Patent No.: US 10,383,594 B2
(45) Date of Patent: Aug. 20, 2019

(54) IMAGE BRIGHTNESS ADJUSTMENT

(71) Applicant: Shenyang Neusoft Medical Systems Co., Ltd., Shenyang (CN)

(72) Inventor: Dexin Wang, Shenyang (CN)

(73) Assignee: SHENYANG NEUSOFT MEDICAL SYSTEMS CO., LTD., Shenyang (CN)

(*) Notice: Subject to any disclaimer, the term of this patent is extended or adjusted under 35 U.S.C. 154(b) by 347 days.

(21) Appl. No.: 15/299,482

(22) Filed: Oct. 21, 2016

(65) Prior Publication Data
US 2017/0150938 A1 Jun. 1, 2017

(30) Foreign Application Priority Data
Dec. 1, 2015 (CN) .......................... 2015 1 0870035

(51) Int. Cl.
A61B 6/00 (2006.01)
(52) U.S. Cl.
CPC .............. *A61B 6/542* (2013.01); *A61B 6/487* (2013.01); *A61B 6/545* (2013.01); *A61B 6/405* (2013.01)
(58) Field of Classification Search
None
See application file for complete search history.

(56) References Cited

U.S. PATENT DOCUMENTS

| | | | |
|---|---|---|---|
| 5,461,658 A | 10/1995 | Joosten | |
| 5,574,764 A | 11/1996 | Granfors et al. | |
| 6,067,343 A | 5/2000 | Brendler et al. | |
| 2014/0348292 A1* | 11/2014 | Yabugami | A61B 5/1075 378/42 |

FOREIGN PATENT DOCUMENTS

| | | |
|---|---|---|
| CN | 1364400 A | 8/2002 |
| CN | 1498093 A | 5/2004 |
| CN | 101382505 A | 3/2009 |
| CN | 102113889 A | 7/2011 |
| CN | 102949193 A | 3/2013 |
| CN | 103211607 A | 7/2013 |
| CN | 103445795 A | 12/2013 |
| CN | 104287750 A | 1/2015 |
| CN | 104394330 A | 3/2015 |
| CN | 105405121 A | 3/2016 |
| EP | 0435528 A2 | 7/1991 |
| EP | 0450970 A2 | 10/1991 |
| EP | 0779770 A | 6/1997 |
| JP | 2015173890 A | 10/2015 |
| WO | 1998048600 A2 | 10/1998 |

* cited by examiner

*Primary Examiner* — Hoon K Song
(74) *Attorney, Agent, or Firm* — Kilpatrick Townsend & Stockton LLP

(57) ABSTRACT

An image brightness adjustment method and an image brightness adjustment device are provided in the present disclosure. A brightness of a fluoroscopic image obtained by irradiating an object with an initial fluoroscopic dose of X-rays is acquired as an initial brightness. A current load corresponding to the initial brightness is determined according to a relationship between image brightness and loads for the initial fluoroscopic dose, where the current load indicates an X-ray blocking ability of the object. Then, a stable fluoroscopic dose corresponding to the current load is determined according to a relationship between load and stable fluoroscopic dose, where the stable fluoroscopic dose is used to obtain a fluoroscopic image of a predetermined brightness for the object.

12 Claims, 6 Drawing Sheets

IMAGE BRIGHTNESS ADJUSTMENT

BACKGROUND

The present disclosure is directed to image brightness adjustment of a medical diagnostic system.

Automatic Brightness Stabilization (ABS) technology is a kind of commonly-used brightness adjustment technology in the field of medical X-ray fluoroscopy. In the case that an initial X-ray dose is fixed, different objects (typically patients) may have different X-ray blocking abilities, and X-rays passing through different objects may have different attenuations. If the X-ray attenuation is higher, it may cause the image brightness too dark. If the X-ray attenuation is lower, it may cause the image brightness too bright. Both of these two cases may result in a blurry image. In order to achieve optimum image brightness, the dose of X-rays may be appropriately adjusted. For example, if the image brightness is too dark, the dose of X-rays may be increased; and if the image brightness is too bright, the dose of X-rays may be decreased. The period of adjustment from starting fluoroscopy to make the fluoroscopic image reach the optimum brightness can be called a fluoroscopy ABS time (hereinafter also referred to as "Stabilization time"), which may be one of key performance indicators for measuring X-ray fluoroscopy. During the stabilization time, the X-ray dose received by the object makes no direct contribution to the fluoroscopic image that eventually stabilizes to the optimum brightness, so the shorter the stabilization time the better.

An X-ray tube (hereinafter called "the tube") is a device for generating X-rays, wherein adjustment of X-ray dose may be implemented by adjustment of fluoroscopic voltage (hereinafter called "fluoroscopic kV") and fluoroscopic current (hereinafter called "fluoroscopic mA"). The fluoroscopic kV may represent a voltage between an anode and a cathode of the X-ray tube, and usually may be 40-150 kV. The fluoroscopic mA may represent a current between the anode and the cathode of X-ray tube, and usually may be 10-30 mA. During the stabilization time, both the fluoroscopic kV and the fluoroscopic mA may need to be adjusted. The adjustment of fluoroscopic kV may be implemented through the following operations: changing an input signal of an Analog-to-digital converter (ADC) of X-ray high voltage generator (hereinafter called "high voltage generator"), and adjusting the fluoroscopic mA by boosting and rectifying of a high voltage tank. As can be seen, the fluoroscopic kV may be adjusted immediately. The fluoroscopic mA may be implemented by the following operations: setting a filament current provided by a high voltage generator to a tube; and heating filament through the filament current to change the temperature of the filament, which may change the amount of electrons emitted from the filament to the tube anode target surface, thereby changing the fluoroscopic mA. The variation of the filament current causing variation of temperature of the filament may be a relatively slow process, which may take about tens to hundreds of milliseconds and may lead to a longer time for adjusting the fluoroscopic mA once.

A proportion, integration, and differentiation (PID) controller may be adopted for achieving the adjustment of the fluoroscopic kV and the fluoroscopic mA. Specifically, after acquiring a non-adjusted fluoroscopic kV and a non-adjusted fluoroscopic mA and acquiring the image brightness obtained by performing X-ray fluoroscopy on the object based on the fluoroscopic kV and the fluoroscopic mA (hereinafter called "initial brightness), these parameters may be inputted into a PID controller, and the adjustment amount of the fluoroscopic kV and the fluoroscopic mA may be determined based on the difference between the initial brightness and the predetermined brightness, thereby achieving the adjustment of the image brightness. However, since each of the adjustment time for adjusting the fluoroscopic mA might not be short, it may cause the overall stabilization time too long.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

The details of one or more embodiments of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

FIG. 3 is a diagram showing a relationship between loads and brightness signal voltage value;

FIG. 4 is a diagram showing a relationship between load and stable fluoroscopic dose when the image brightness stabilizes at the optimum brightness;

DETAILED DESCRIPTION

As described above, when adopting PID control method for adjusting the brightness of the fluoroscopic image, stabilization time may be longer, and thus improvement is necessary. For this reason, an image brightness adjustment mechanism is provided in the present disclosure. Before the beginning of fluoroscopy, a relationship curve between initial brightness and a corresponding load and a relationship curve between loads and a stable fluoroscopic dose when image brightness stabilizes at the optimum brightness may be calibrated; and after the beginning of fluoroscopy, a load of an object may be obtained according to the relationship curve between the initial brightness and the load, and the stable fluoroscopic dose corresponding to the object may be obtained according to the relationship curve between loads and a stable fluoroscopic dose. Thus, through adjusting an initial fluoroscopic dose of an X-ray generating device (may be embodied as an X-ray high voltage generator) to the stable fluoroscopic dose, the brightness of the generated fluoroscopic image may basically reach the optimum brightness.

Figure 1:
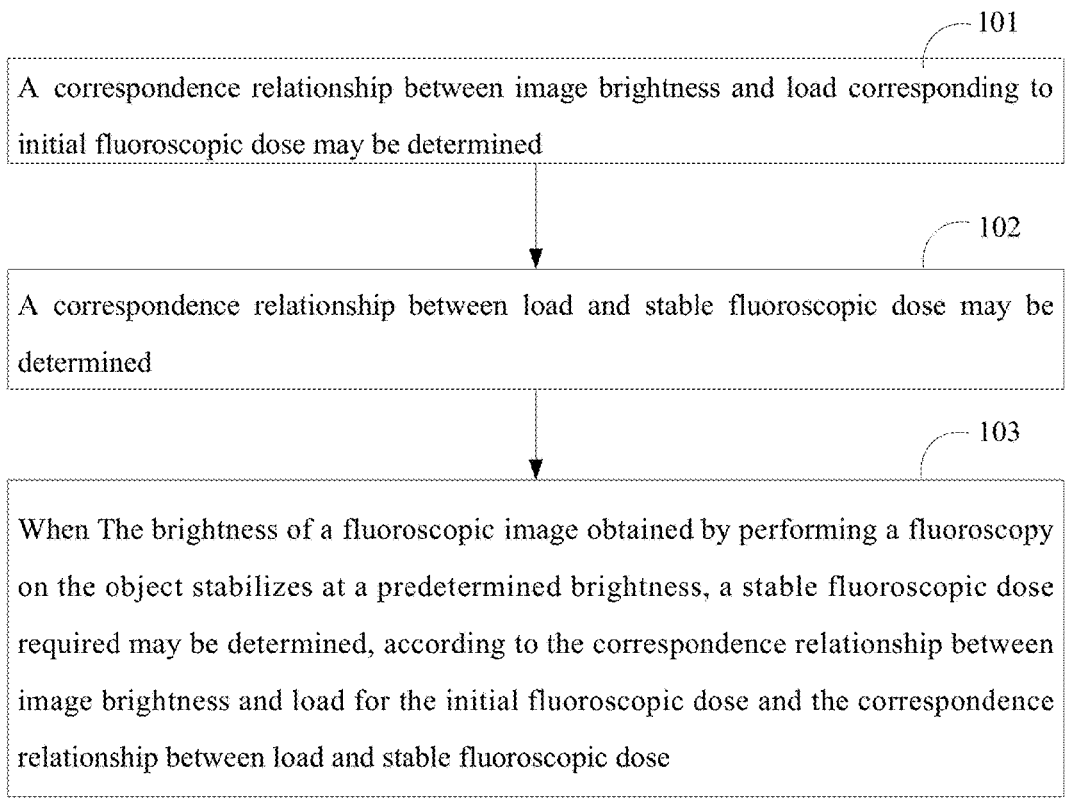
FIG. 1 is a flowchart illustrating the operating procedures of an image brightness adjustment method according to an example of the present disclosure.

Referring to FIG. 1, FIG. 1 provides an image brightness adjustment method based on the above major concerns. As shown in FIG. 1, the method may mainly include the following blocks.

At block 101, a relationship between image brightness and loads for an initial fluoroscopic dose may be determined.

Before performing fluoroscopy on the object, a curve capable of reflecting a relationship between image brightness and loads for the initial fluoroscopic dose may be determined. The initial fluoroscopic dose may include an initial fluoroscopic kV and an initial fluoroscopic mA. In practical application, values of these two parameters may be selected as needed. For example, the initial fluoroscopic kV may be 60 kV, and the initial fluoroscopic mA may be 15 mA.

The block 101 for determining the relationship between image brightness and loads for the initial fluoroscopic dose may mainly include the following specific steps.

Figure 2:
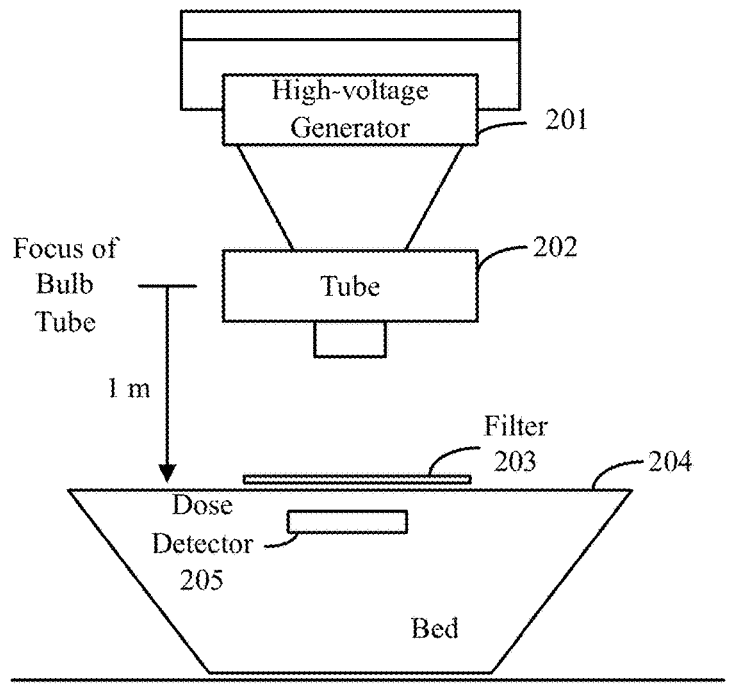
FIG. 2 is a schematic diagram of an X-ray diagnostic system.

First, referring to FIG. 2. A bed 204 of an X-ray diagnostic system (such as, an RF X-ray machine) may be laid flat, a fluoroscopic dose of an X-ray high voltage generator 201 may be set to the initial fluoroscopic dose, and a distance between a focus of an X-ray tube 202 and an upper surface of the bed 204 may be adjusted. According to an example, the distance may be adjusted to be, for example, 1 meter, since this height is the most common height for examining patients.

Figures 3, 4:
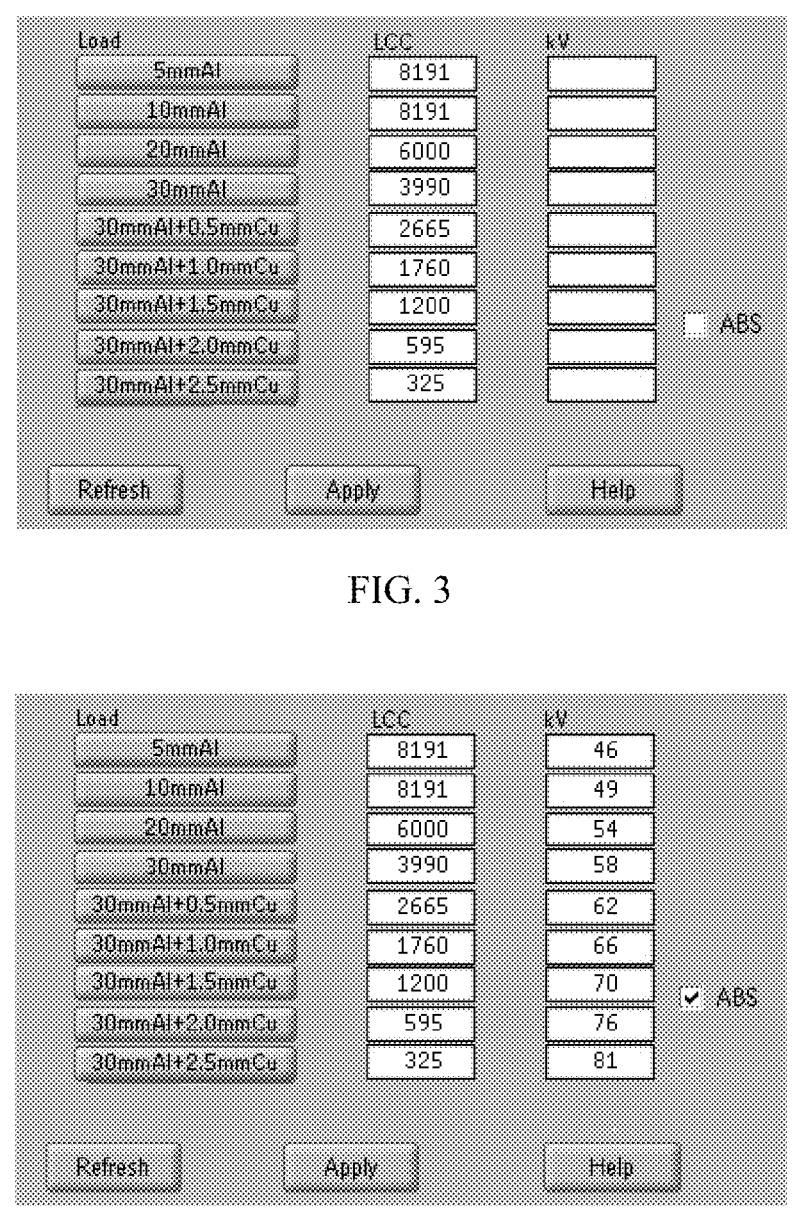

Next, the X-ray high voltage generator 201 may be set in a non-ABS adjustment mode. Under the non-ABS adjustment mode, an adjustment on the image brightness is not automatically performed. Then, filters 203 with different sizes of loads may be separately placed on the upper surface of the bed 204, and a fluoroscopy may be performed on the filters 203 respectively. Herein, the size of load means the X-ray blocking ability of the object, and usually may be measured by "mmAl" or "mmCu". 1 mmAl is equivalent to the X-ray blocking ability of a 1 mm thick aluminium plate, and 1 mmCu is equivalent to the X-ray blocking ability of a 1 mm thick copper plate. In this example, the filter 203 may be an aluminium plate or a copper plate with a certain thickness. A brightness signal voltage value corresponding to the load of the filter may be obtained based on a brightness signal detected by a dose detector 205. FIG. 3 is a diagram showing the different sizes of loads and the corresponding brightness signals voltage values (LCC). For example, the corresponding brightness signal voltage value of a 5 mm thick aluminium plate is 8191 mV, the corresponding brightness signal voltage value of superimposing a 30 mm thick aluminium plate together with a 0.5 mm thick copper plate is 2665 mV.

Then, a curve established based on the above-described relationship between a load and a brightness signal voltage value may be used as a relationship curve between load and image brightness. Certainly, in another example, after obtaining the brightness signal, the specific value of the image brightness may be determined according to the brightness signal voltage value, and then the corresponding relationship curve between load and image brightness may be obtained. Herein, in order to facilitate calculation, the brightness signal voltage value is used to indicate the specific value of the image brightness.

At block 102, a relationship between load and stable fluoroscopic dose may be determined.

According to an example, the relationship between load and stable fluoroscopic dose may be determined based on the following operations. First, as described above, the bed 204 of the X-ray diagnostic system (such as, an RF X-ray machine) may be laid flat, a fluoroscopic dose of the X-ray high voltage generator 201 may be set to the initial fluoroscopic dose, and the distance between a focus of the X-ray tube 202 and an upper surface of the bed 204 may be adjusted to, for example, 1 meter.

Next, the X-ray high voltage generator 201 may be set in an ABS adjustment mode. Under the ABS adjustment mode, adjustment on the image brightness may be automatically performed by using a PID control method. Then, the above-described filters 203 with different sizes of loads may be separately placed on the upper surface of the bed 204, and a fluoroscopy may be performed on the filters 203, respectively. When the obtained image brightness stabilizes at predetermined brightness, the stable fluoroscopic dose may be determined, including the value of the stable fluoroscopic kV. FIG. 4 is a diagram showing different sizes of loads and corresponding stable fluoroscopic kVs. For example, the corresponding stable fluoroscopic kV of a 5 mm thick aluminium plate is 46 kV, and the corresponding stable fluoroscopic kV of superimposing a 30 mm thick aluminium plate together with a 0.5 mm thick copper plate is 62 kV.

Then, the relationship curve may be obtained according to the relationship between different loads and their stable fluoroscopic kVs. The relationship between stable fluoroscopic kV and stable fluoroscopic mA may be obtained by inquiring a kV-mA table. For example, please refer to Table 1, which is the kV-mA table. The stable fluoroscopic mA corresponding to the stable fluoroscopic kV may be directly searched from the Table 1. If the specific stable fluoroscopic mA is not in the Table 1, select two values that are closest to the specific stable fluoroscopic kV and determine through interpolation algorithm so as to obtain the corresponding specific stable fluoroscopic mA. For example, if the specific fluoroscopic kV is 45 kV, the two closest values are 40 kV and 50 kV. Since the stable fluoroscopic mA corresponding to 40 kV is 10 mA and the stable fluoroscopic mA corresponding to 50 kV is 12 mA, the stable fluoroscopic mA corresponding to 45 kV is 11 mA.

TABLE 1

| kV | 40 | 50 | 60 | 70 | 80 | 90 | 100 | 110 | 120 |
|---|---|---|---|---|---|---|---|---|---|
| mA | 10 | 12 | 15 | 18 | 21 | 25 | 30 | 30 | 30 |

The stable fluoroscopic dose may be determined through determining the stable fluoroscopic kV and the stable fluoroscopic mA.

At block 103, when the brightness of a fluoroscopic image obtained by performing a fluoroscopy on the object stabilizes at a predetermined brightness, a stable fluoroscopic dose required may be determined, according to the relationship between image brightness and loads for the initial fluoroscopic dose and the relationship between load and stable fluoroscopic dose.

Figure 5:
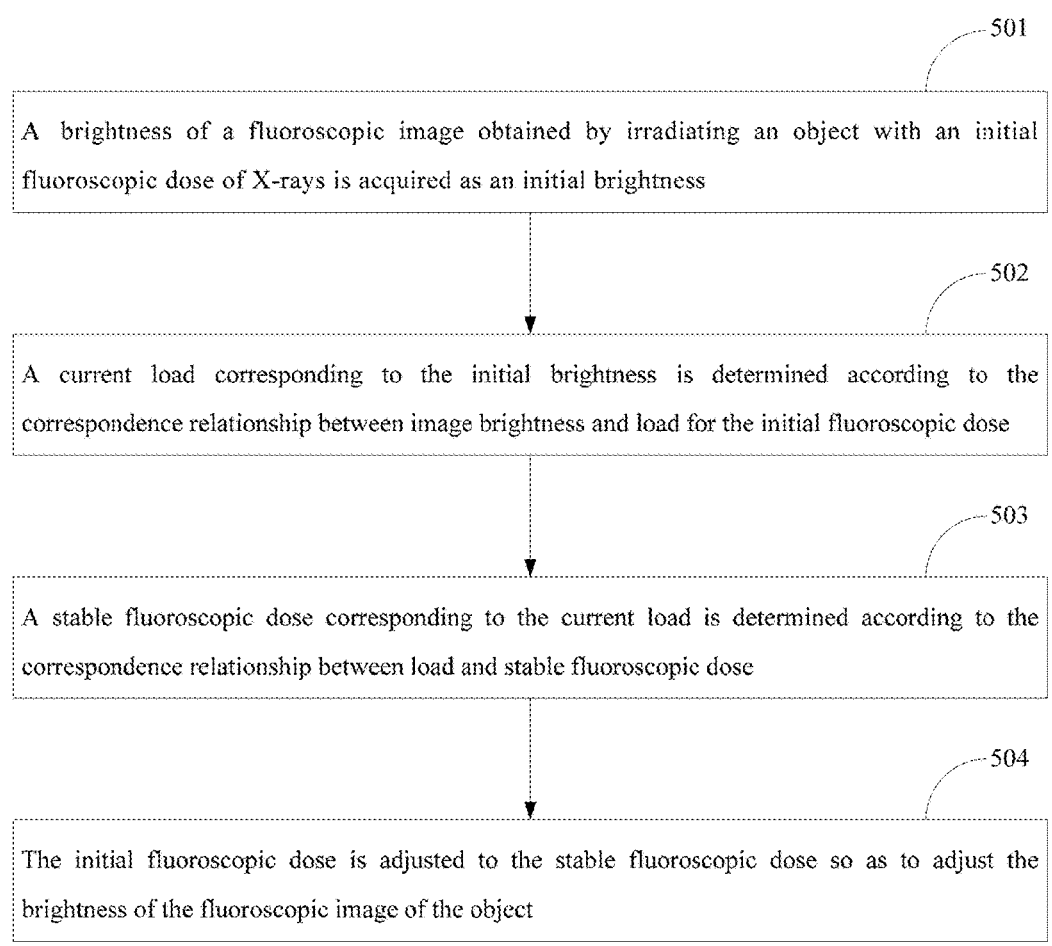
FIG. 5 is a flowchart illustrating the operating procedures of an image brightness adjustment method according to another example of the present disclosure.

Referring to FIG. 5, FIG. 5 is a flowchart illustrating an image brightness adjustment method, which shows the specific steps for performing an image brightness adjustment method by using the relationship between image brightness and loads for the initial fluoroscopic dose and the relationship between load and stable fluoroscopic dose. As shown in FIG. 5, the method may include the following blocks.

At block 501, a brightness of a fluoroscopic image obtained by irradiating an object with an initial fluoroscopic dose of X-rays is acquired as an initial brightness.

For the same load, different fluoroscopic doses may obtain different image brightness. Therefore, in order to determine the load of the object according to the initial brightness of the fluoroscopic image obtained by X-rays irradiation, the fluoroscopy may be performed on the object with the initial fluoroscopic dose of X-rays.

At block 502, a current load corresponding to the initial brightness is determined according to the relationship between image brightness and loads for the initial fluoroscopic dose.

After acquiring the initial brightness of the object, the current load (i.e. an X-ray blocking ability of the object) corresponding to the initial brightness may be determined according to the relationship between image brightness and loads for the initial fluoroscopic dose.

In an example, the initial brightness may be represented by a brightness signal voltage value. Referring to FIG. 3, for example, assuming that the obtained brightness signal voltage value is 3990 mV, the load of the corresponding object may be equivalent to a load of a 30 mm thick aluminium plate.

At block 503, a stable fluoroscopic dose corresponding to the current load is determined according to the relationship between load and stable fluoroscopic dose.

After the load of the object is determined, the stable fluoroscopic dose corresponding to the load of the object may be determined according to the relationship between load and stable fluoroscopic dose.

In the example above, assuming that the load of the object is determined to be equivalent to the load of a 30 mm thick aluminium plate, the corresponding stable fluoroscopic kV of the object may be determined as 58 kV based on the relationship between load and stable fluoroscopic dose shown in FIG. 4. In addition, after determining the value of the stable fluoroscopic kV, the value of the stable fluoroscopic mA may be determined based on the conversion relationship between stable fluoroscopic kV and stable fluoroscopic mA.

At block 504, the initial fluoroscopic dose is adjusted to the stable fluoroscopic dose so as to adjust the brightness of the fluoroscopic image of the object.

After determining the corresponding stable fluoroscopic kV and stable fluoroscopic mA of the object, the initial fluoroscopic kV may be adjusted to the stable fluoroscopic kV and the initial fluoroscopic mA to the stable fluoroscopic mA. Since the initial fluoroscopic dose is adjusted to the stable fluoroscopic dose when the image brightness stabilizes at the predetermined optimum brightness, an adjustment of the image brightness may be achieved.

Compared with the adjustment scheme of adopting PID closed-loop control technology for adjusting the fluoroscopic dose based on the difference between an actual image brightness and a predetermined image brightness, the adjustment scheme of combining two relationship s to directly obtain the stable fluoroscopic dose of the object may effectively reduce the stabilization time required for stabilizing the fluoroscopic image to the optimum brightness, thereby reducing X-ray damages to patients and saving X-ray dose.

Figure 6:
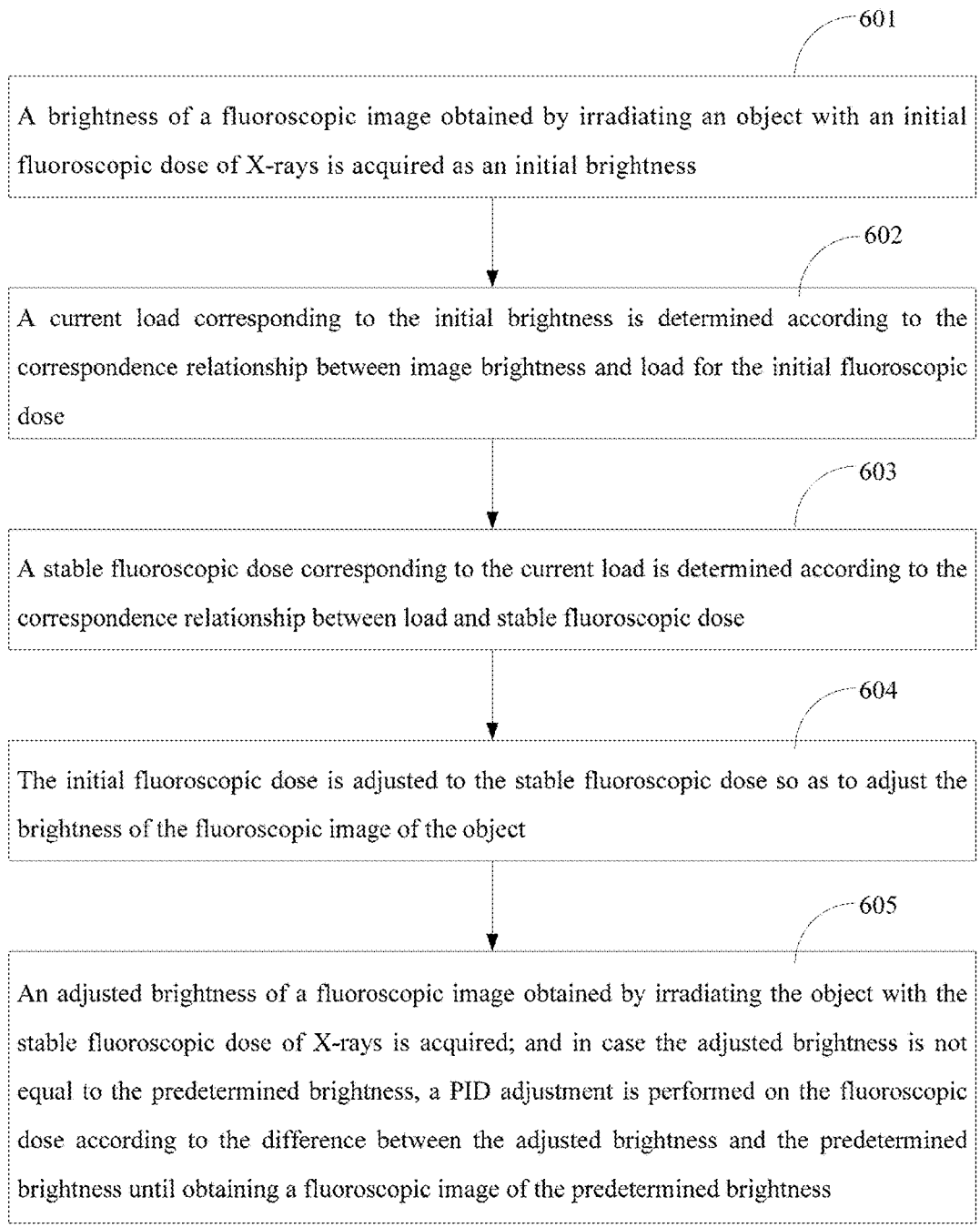
FIG. 6 is a flowchart illustrating the operating procedures of an image brightness adjustment method according to still another example of the present disclosure.

Be noted that, the above-described stable fluoroscopic dose is obtained according to the above-described two relationships, and the fluoroscopic image obtained with the stable fluoroscopic dose may simply basically reach the predetermined image brightness. In other words, there may be some error exists between the actual image brightness obtained with the stable fluoroscopic dose and the predetermined image brightness. According to another example, in order to narrow the difference between the actual image brightness and the predetermined image brightness, after the initial fluoroscopic dose is adjusted to the stable fluoroscopic dose, the PID control method may be adopted to fine-tune the image brightness for further improving the adjustment accuracy of the image brightness. Referring to FIG. 6, the image brightness adjustment method may mainly include the following blocks.

The blocks 601-604 may be consistent with the blocks 501-504 respectively, and further description is omitted herein.

At block 605, an adjusted brightness of a fluoroscopic image obtained by irradiating the object with the stable fluoroscopic dose of X-rays is acquired; and in case the adjusted brightness is not equal to the predetermined brightness, a PID adjustment is performed on the fluoroscopic dose according to the difference between the adjusted brightness and the predetermined brightness until obtaining a fluoroscopic image of the predetermined brightness.

Although different loads correspond to different initial brightness, the optimum brightness (i.e., the predetermined brightness) of image is basically the same. Compared with the initial brightness, the brightness of the image obtained by adjusting to the stable fluoroscopic dose has a smaller difference with the predetermined brightness. Hence, the time required for using PID control method to fine-tune the fluoroscopic dose may be less, thereby may stabilize the image brightness to the predetermined brightness quickly and accurately.

Below, experimental data is used for proving advantages of the technical scheme provided in the present disclosure. Before proving, two concepts are introduced first: continuous fluoroscopy and pulsed fluoroscopy. The continuous fluoroscopy represents a fluoroscopy manner for continuously generating X-rays and then forming a continuous image. The pulsed fluoroscopy represents a fluoroscopy manner for generating X-ray pulses in a certain frequency (such as, 3 frames/sec or 15 frames/sec) and forming a discontinuous image. Compared with the continuous fluoroscopy, the pulsed fluoroscopy has the advantage of lowering X-ray radiation dose and may change the continuous property of the fluoroscopic image through adjusting frame rate (pulse frequency). The image brightness adjustment scheme provided in the present disclosure may be applied to the continuous fluoroscopy and the pulsed fluoroscopy, but has a more apparent improving effect to the pulsed fluoroscopy. The experimental data provided below are experimental data based on pulsed-fluoroscopy. Referring to Table 2, Table 2 shows test data obtained by using PID scheme and the scheme of the present disclosure separately in an Iconia RF high voltage generator.

TABLE 2

| First Filter | Second Filter | Stabilization Frame Number for PID Scheme | Stabilization Frame Number for Scheme of the Present Disclosure | Frame Number Saved in Scheme of the Present Disclosure |
|---|---|---|---|---|
| 5 mm Al | 10 mm Al | 3 | 3 | 0 |
| 10 mm Al | 25 mm Al | 5 | 3 | 2 |
| 25 mm Al | 25 mm Al + 2.5 mm Cu | 8 | 3 | 5 |
| 25 mm Al | 35 mm Al | 6 | 3 | 3 |
| 35 mm Al | 35 mm Al + 2.5 mm Cu | 7 | 3 | 4 |
| 35 mm Al + 2.5 mm Cu | 25 mm Al + 2.5 mm Cu | 4 | 2 | 2 |
| 25 mm Al + 2.5 mm Cu | 30 mm Al | 6 | 3 | 3 |
| 30 mm Al | 25 mm Al | 2 | 2 | 0 |
| 25 mm Al | 5 mm Al | 5 | 2 | 3 |
| 5 mm Al | 35 mm Al + 2.5 mm Cu | 13 | 4 | 9 |
| 35 mm Al + 2.5 mm Cu | 5 mm Al | 11 | 3 | 8 |
| 30 mm Al | 30 mm Al | 0 | 0 | 0 |

In Table 2, the first column and the second column represent variations of loads, i.e., the object is changed from a first filter to a second filter. In general, the image brightness may change with the variation of loads, and thus an adjustment to the fluoroscopic dose is required. As can be seen from the third column to the fifth column, although an adjustment must be started from the initial fluoroscopic dose each time the load changes by using the scheme of the present disclosure, compared with the time spent by PID scheme in adjusting the fluoroscopic dose, the frame number of the scheme of the present disclosure is significantly less. The larger the variation of the load, the more apparent the improving effect of the scheme of the present disclosure.

For example, regarding to passing through a first filter of a 5 mm thick aluminium plate and then passing through a second filter of a 35 mm thick aluminium plate superimposed together with a 2.5 mm thick copper plate, there is no need to adjust the fluoroscopic dose to the initial fluoroscopic dose after performing a fluoroscopy on the first filter if PID adjustment method is adopted, and an adjustment is directly performed on the fluoroscopic dose used for performing the fluoroscopy on the first filter. Then the frame number required for reaching the optimum image brightness is 13 frames. If the technical scheme of the present disclosure is adopted, the fluoroscopic dose is adjusted to the initial fluoroscopic dose after performing the fluoroscopy on the first filter. Since the adjustment is started from the initial fluoroscopic dose, the frame number required for reaching the optimum image brightness is 4 frames, wherein the first frame is used for acquiring the initial brightness of the object. Next, the gap between the first frame and the second frame may be used for calculating the corresponding stable fluoroscopic dose of the object, and a second frame pulse of X-rays may be generated using the stable fluoroscopic dose. Then, the third frame and the fourth frame may be used for fine-tuning. As can be seen, by adopting the image brightness adjustment method of the present disclosure, a total time of about 9 frames may be saved compared with adopting the PID method, thereby may effectively save the stabilization time of image brightness.

Based on the above-described image brightness adjustment method provided in the above examples, an image brightness adjustment device is provided in the example of the present disclosure.

Figure 7:
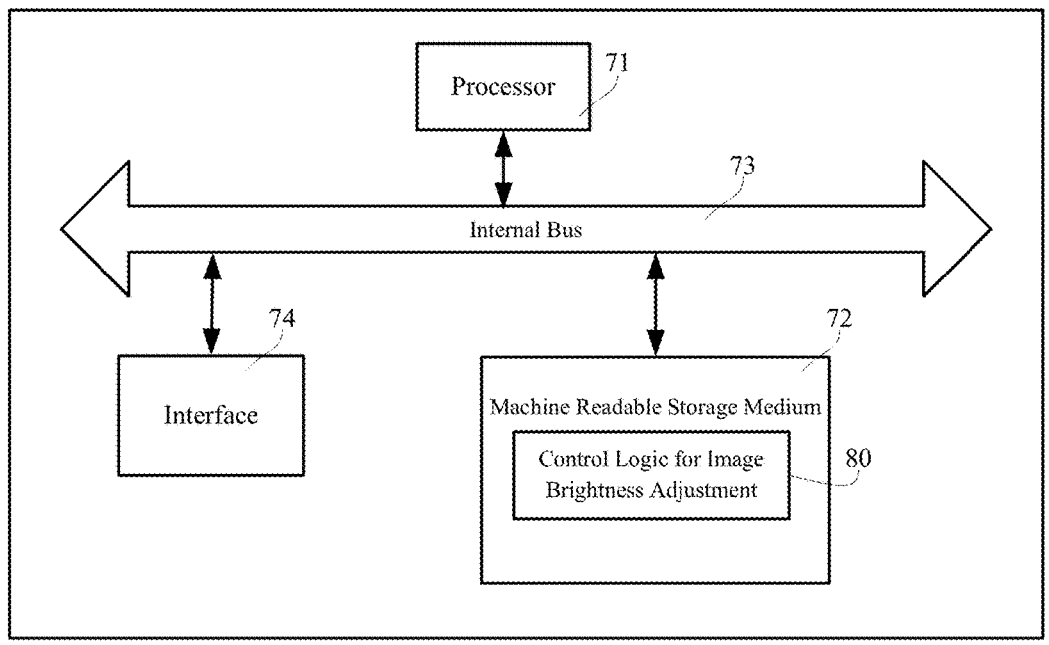
FIG. 7 is a hardware architecture diagram of an image brightness adjustment device according to an example of the present disclosure.
Figure 8:
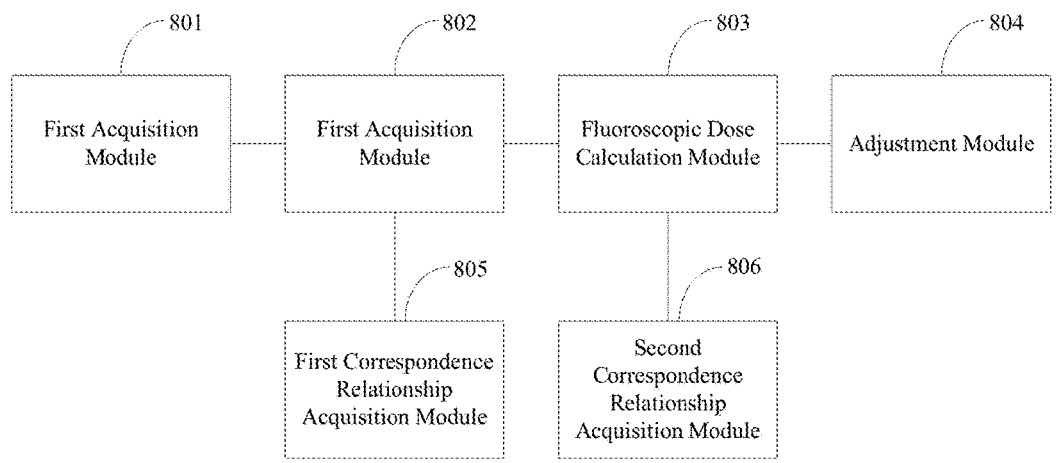
FIG. 8 is a block diagram of a function module of control logic for an image brightness adjustment according to an example of the present disclosure.

Referring to FIG. 7, FIG. 7 is a hardware architecture diagram of an image brightness adjustment device according to the present disclosure. As shown in FIG. 7, the image brightness adjustment device may include a processor 71 and a machine readable storage medium 72, wherein the processor 71 is coupled to the machine readable storage medium 72 through an internal bus 73. In other possible implementations, the image brightness adjustment device may further include an external interface 74 for communicating with other devices or components.

In different examples, the machine readable storage medium 72 may be Radom Access Memory (RAM), volatile memory, non-volatile memory, flash memory, storage drives (such as, a hard drive), solid state drive, storage disks of any type (such as, CD-ROM, DVD, etc.), or similar storage medium, or a combination thereof.

Further, the machine readable storage medium 72 may store a control logic 80 for image brightness adjustment. Divided according to function, the control logic 80 may include a first acquisition module 801, a load calculation module 802, a fluoroscopic dose calculation module 803, and an adjustment module 804. The first acquisition module 801 is connected to the load calculation module 802, the load calculation module 802 is connected to the fluoroscopic dose calculation module 803, and the fluoroscopic dose calculation module 803 is connected to the adjustment module 804.

The first acquisition module 801 is used for acquiring a brightness of a fluoroscopic image obtained by irradiating an object with an initial fluoroscopic dose of X-rays as an initial brightness.

The load calculation module 802 is used for determining a current load corresponding to the initial brightness according to a relationship between image brightness and loads for the initial fluoroscopic dose, where the current load indicates an X-ray blocking ability of the object.

The fluoroscopic dose calculation module 803 is used for determining a stable fluoroscopic dose corresponding to the current load according to the relationship between load and stable fluoroscopic dose, where a fluoroscopic image of a predetermined brightness may be obtained for the object with the stable fluoroscopic dose.

The adjustment module 804 is used for adjusting the initial fluoroscopic dose to the stable fluoroscopic dose, and irradiating the object with the stable fluoroscopic dose of X-rays.

In this example, after acquiring the initial brightness of a fluoroscopic image obtained by irradiating an object with an initial fluoroscopic dose of X-rays, the stable fluoroscopic dose corresponding to the load of the object may be obtained according to the relationship between image brightness and loads for the initial fluoroscopic dose as well as the relationship between load and stable fluoroscopic dose. Therefore, the brightness of the fluoroscopic image of the object may basically reach the optimum brightness through one adjustment, thereby greatly shortening the stabilization time of image brightness adjustment.

In addition, according to an example, the control logic 80 may further include a first correspondence relationship acquisition module 805, which is connected to the load calculation module 802. The first correspondence relationship acquisition module 805 is used for: acquiring image brightness by irradiating a plurality of loads with the initial fluoroscopic dose of X-rays respectively under a non-ABS adjustment mode; and determining the relationship between image brightness and loads for the initial fluoroscopic dose based on the plurality of loads and the corresponding acquired image brightness.

According to another example, the control logic 80 may further include a second correspondence relationship acquisition module 806, which is connected to the fluoroscopic dose calculation module 803. The fluoroscopic dose calculation module 803 is used for: acquiring a plurality of stable fluoroscopic doses corresponding to a plurality of loads respectively by performing a PID adjustment method under an ABS adjustment mode; and determining the relationship between load and stable fluoroscopic dose based on the plurality of loads and the corresponding acquired stable fluoroscopic doses.

In addition, the initial fluoroscopic dose may include an initial fluoroscopic mA and an initial fluoroscopic kV, and the stable fluoroscopic dose may include a stable fluoroscopic kV and a stable fluoroscopic mA. In this case, the relationship between load and stable fluoroscopic dose may include the relationship between load and stable fluoroscopic kV. And, the fluoroscopic dose calculation module 803 is specifically used for: determining the stable fluoroscopic kV corresponding to the current load according to the relationship between load and stable fluoroscopic kV; and calculating the stable fluoroscopic mA corresponding to the stable fluoroscopic kV according to a conversion relationship between stable fluoroscopic kV and stable fluoroscopic mA.

Figure 9:
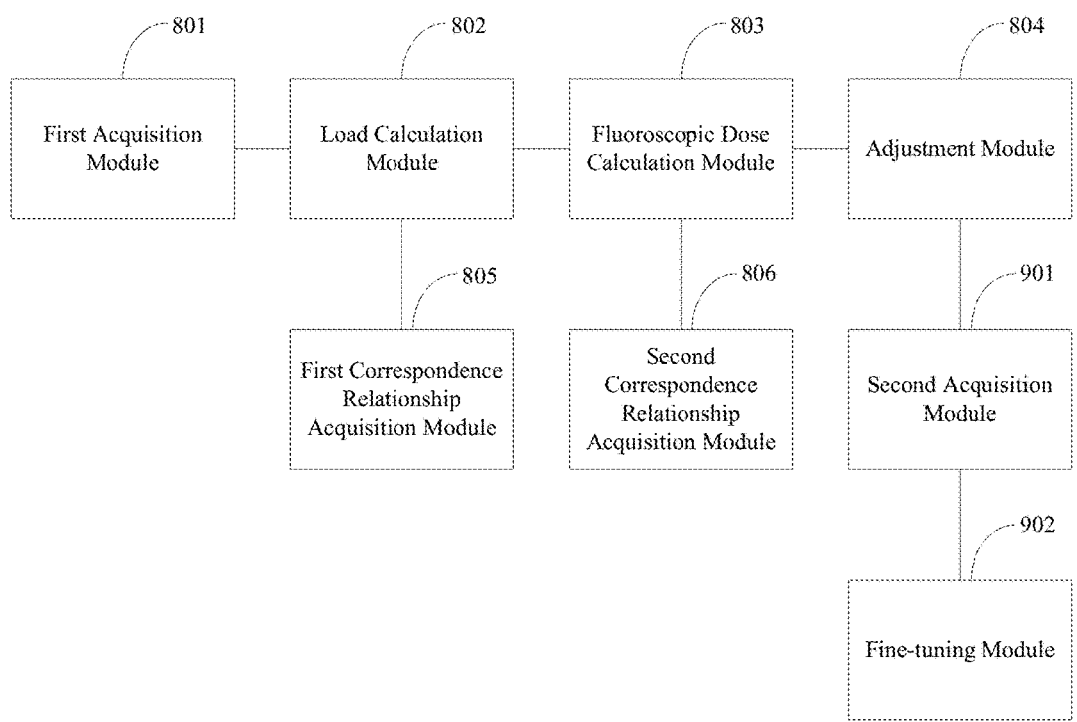
FIG. 9 is a block diagram of a function module of control logic for an image brightness adjustment according to another example of the present disclosure.

In order to achieve the effect of improving the accuracy of image brightness adjustment, another example is provided in the present disclosure. Referring to FIG. 9, the control logic 80 for image brightness adjustment provided in the example may further include a second acquisition module 901 and a fine-tuning module 902, wherein the adjustment module 804 is connected to the second acquisition module 901 and the second acquisition module 901 is connected to the fine-tuning module 902. The second acquisition module 901 is used for acquiring a brightness of a fluoroscopic image obtained by irradiating the object with the stable fluoroscopic dose of X-rays as an adjusted brightness. The fine-tuning module 902 is used for: in case the adjusted brightness is not equal to the predetermined brightness, performing a PID adjustment according to the difference between the adjusted brightness and the predetermined brightness until obtaining a fluoroscopic image of the predetermined brightness with respect to the object.

By using the PID adjustment for fine-tuning the image brightness, the accuracy of image brightness adjustment may be improved effectively.

The image brightness adjustment device of the present disclosure may be applied in an RF (Radiography and Fluoroscopy) system or any electronic device equipped with a processor (especially an image processor). The electronic device may be any existing, under development, or to be developed in future electronic device, which may include but is not limited to, any existing, under development, or to be developed in future desktop computer, laptop computer, mobile terminal (including smartphones, non-smartphones, a variety of tablet PCs) and the like. The example of the device may be implemented by software, or hardware, or a combination thereof. In an example of implemented with software, as a device in logical sense, it is formed by using the processor of the RF system or the electronic device equipped with the processor to read from corresponding computer program instructions stored in a storage into memory to run.

The example below is implemented with software, further describes how the image brightness adjustment device runs the control logic 80. In this example, the control logic 80 of the present disclosure should be understood as machine readable instructions stored in the machine readable storage medium 72. When the processor 71 of the image brightness adjustment device executes the control logic 80, by invoking the corresponding machine readable instructions of the control logic 80 stored in the machine readable storage medium 72, the processor 71 is caused to:

acquire a brightness of a fluoroscopic image obtained by irradiating an object with an initial fluoroscopic dose of X-rays as an initial brightness;

determine a current load corresponding to the initial brightness according to a relationship between image brightness and loads for the initial fluoroscopic dose, wherein the current load indicates an X-ray blocking ability of the object;

determine a stable fluoroscopic dose corresponding to the current load according to a relationship between load and stable fluoroscopic dose, wherein the stable fluoroscopic dose represents a fluoroscopic dose required for obtaining a fluoroscopic image of the object when the image brightness stabilizes at a predetermined brightness; and irradiate the object according to the stable fluoroscopic dose of X-rays.

In an example, the initial fluoroscopic dose may include an initial fluoroscopic mA and an initial fluoroscopic kV, and the stable fluoroscopic dose may include a stable fluoroscopic kV and a stable fluoroscopic mA.

According to an example, said machine readable instructions further cause the processor to: acquire a plurality of image brightness by irradiating a plurality of loads with the initial fluoroscopic dose of X-rays respectively under a non-ABS adjustment mode; and determine the relationship between image brightness and loads for the initial fluoroscopic dose based on the plurality of loads and corresponding acquired image brightness.

According to an example, said machine readable instructions further cause the processor to: acquire a plurality of stable fluoroscopic doses corresponding to a plurality of loads respectively by performing a PID adjustment method under an ABS adjustment mode; and determine the relationship between load and stable fluoroscopic dose based on the plurality of loads and corresponding acquired stable fluoroscopic doses.

According to another example, said machine readable instructions further cause the processor to: acquire a brightness of a fluoroscopic image obtained by irradiating the object with the stable fluoroscopic dose of X-rays as an adjusted brightness; and in case the adjusted brightness is not equal to the predetermined brightness, perform a PID adjustment according to the difference between the adjusted brightness and the predetermined brightness until obtaining a fluoroscopic image of the predetermined brightness with respect to the object.

According to an example, the relationship between load and stable fluoroscopic dose may include the relationship between load and stable fluoroscopic kV. In this case, when determining the stable fluoroscopic dose corresponding to the current load according to the relationship between load and stable fluoroscopic dose, said machine readable instructions further cause the processor to: determine a stable fluoroscopic kV corresponding to the current load according to the relationship between load and stable fluoroscopic kV; and determine the stable fluoroscopic mA corresponding to the stable fluoroscopic kV according to the conversion relationship between stable fluoroscopic kV and stable fluoroscopic mA.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An image brightness adjustment method, comprising:
acquiring image brightness of a fluoroscopic image as an initial brightness, the fluoroscopic image being obtained by irradiating an object with an initial fluoroscopic dose of X-rays;
determining a current load corresponding to the initial brightness according to a relationship between image brightness and loads being obtained based on the initial fluoroscopic dose, wherein the current load indicates an X-ray blocking ability of the object;
determining a stable fluoroscopic dose corresponding to the current load according to a relationship between loads and stable fluoroscopic dose, wherein the stable fluoroscopic dose is used to obtain a fluoroscopic image of a predetermined brightness for the object; and
irradiating the object with the stable fluoroscopic dose of X-rays.

2. The method according to claim 1, further comprising:
acquiring image brightness by irradiating a plurality of loads with the initial fluoroscopic dose of X-rays respectively under a non-ABS adjustment mode; and
determining the relationship between image brightness and loads being obtained based on the initial fluoroscopic dose with the plurality of loads and corresponding acquired image brightness.

3. The method according to claim 1, further comprising:
acquiring a plurality of stable fluoroscopic doses corresponding to a plurality of loads respectively by performing a proportion, integration, and differentiation (PID) adjustment under an ABS adjustment mode; and
determining the relationship between loads and stable fluoroscopic dose based on the loads and corresponding acquired stable fluoroscopic doses.

4. The method according to claim 1, further comprising:
acquiring a brightness of a fluoroscopic image obtained by irradiating the object with the stable fluoroscopic dose of X-rays as an adjusted brightness; and
when the adjusted brightness is not equal to the predetermined brightness, performing a PID adjustment according to a difference between the adjusted brightness and the predetermined brightness until obtaining a fluoroscopic image of the predetermined brightness with respect to the object.

5. The method according to claim 1, wherein:
the initial fluoroscopic dose comprises an initial fluoroscopic mA and an initial fluoroscopic kV; and
the stable fluoroscopic dose comprises a stable fluoroscopic kV and a stable fluoroscopic mA.

6. The method according to claim 5, wherein:
the relationship between loads and stable fluoroscopic dose comprises a relationship between loads and stable fluoroscopic kV; and
determining the stable fluoroscopic dose corresponding to the current load according to the relationship between loads and stable fluoroscopic dose, comprises:
determining a stable fluoroscopic kV corresponding to the current load according to the relationship between loads and stable fluoroscopic kV; and
determining a stable fluoroscopic mA corresponding to the stable fluoroscopic kV according to a conversion relationship between stable fluoroscopic kV and stable fluoroscopic mA.

7. An image brightness adjustment device, the device comprising:
a processor;
a storage medium, which stores executable machine readable instructions for the processor;
wherein, by reading and performing the machine readable instructions, the processor is caused to:
acquire image brightness of a fluoroscopic image as an initial brightness, the fluoroscopic image being obtained by irradiating an object with an initial fluoroscopic dose of X-rays;
determine a current load corresponding to the initial brightness according to a relationship between image brightness and loads being obtained based on the initial fluoroscopic dose, wherein the current load indicates an X-ray blocking ability of the object;
determine a stable fluoroscopic dose corresponding to the current load according to a relationship between loads and stable fluoroscopic dose, wherein the stable fluoroscopic dose is used to obtain a fluoroscopic image of a predetermined brightness for the object; and
irradiate the object with the stable fluoroscopic dose of X-rays.

8. The device according to claim 7, wherein said machine readable instructions further cause the processor to:
acquire image brightness by irradiating a plurality of loads with the initial fluoroscopic dose of X-rays respectively under a non-ABS adjustment mode; and
determine the relationship between image brightness and loads being based on the initial fluoroscopic dose with the plurality of loads and corresponding acquired image brightness.

9. The device according to claim 7, wherein said machine readable instructions further cause the processor to:
acquire a plurality of stable fluoroscopic doses corresponding to a plurality of loads respectively by performing a PID adjustment method under an ABS adjustment mode; and
determine the relationship between loads and stable fluoroscopic dose based on the plurality of loads and corresponding acquired stable fluoroscopic doses.

10. The device according to claim 7, wherein said machine readable instructions further cause the processor to:
acquire a brightness of a fluoroscopic image obtained by irradiating the object with the stable fluoroscopic dose of X-rays as an adjusted brightness; and
when the adjusted brightness is not equal to the predetermined brightness, perform a PID adjustment according to a difference between the adjusted brightness and the predetermined brightness until obtaining a fluoroscopic image of the predetermined brightness with respect to the object.

11. The device according to claim 7, wherein:
the initial fluoroscopic dose comprises an initial fluoroscopic mA and an initial fluoroscopic kV; and
the stable fluoroscopic dose comprises a stable fluoroscopic kV and a stable fluoroscopic mA.

12. The device according to claim 11, wherein:
the relationship between loads and stable fluoroscopic dose comprises a relationship between loads and stable fluoroscopic kV; and
when determining the stable fluoroscopic dose corresponding to the current load according to the relationship between loads and stable fluoroscopic dose, said machine readable instructions further cause the processor to:
determine a stable fluoroscopic kV corresponding to the current load according to the relationship between loads and stable fluoroscopic kV; and
determine a stable fluoroscopic mA corresponding to the stable fluoroscopic kV according to a conversion relationship between stable fluoroscopic kV and stable fluoroscopic mA.

\* \* \* \* \*